United States Patent
Bright et al.

(10) Patent No.: US 11,624,672 B2
(45) Date of Patent: Apr. 11, 2023

(54) APPARATUS AND METHOD FOR AUTOMATIC LEAK DETECTION

(71) Applicant: ATEQ, Les Clayes sous Bois (FR)

(72) Inventors: Brian D. Bright, London (CA); Davy Leboucher, Bloomfield Hills, MI (US)

(73) Assignee: ATEQ, Les Clayes sous Bois (FR)

( * ) Notice: Subject to any disclaimer, the term of this patent is extended or adjusted under 35 U.S.C. 154(b) by 326 days.

(21) Appl. No.: 16/909,691

(22) Filed: Jun. 23, 2020

(65) Prior Publication Data

US 2021/0396622 A1    Dec. 23, 2021

(51) Int. Cl.
*G01M 3/04* (2006.01)
*G01N 33/00* (2006.01)

(52) U.S. Cl.
CPC ............ *G01M 3/04* (2013.01); *G01N 33/005* (2013.01)

(58) Field of Classification Search
CPC .......... G01M 3/02; G01M 3/20; G01M 3/202; G01M 3/22; G01M 3/221; G01M 3/222; G01M 3/223; G01M 3/224; G01M 3/225; G01M 3/226; G01M 3/227; G01M 3/228; G01M 3/229; G01M 3/26
USPC .................................................... 73/40–49.8
See application file for complete search history.

(56) References Cited

U.S. PATENT DOCUMENTS

| | | | | |
|---|---|---|---|---|
| 2,669,660 A | * | 2/1954 | Gambrill | G01M 3/229 250/289 |
| 2,679,747 A | * | 6/1954 | Andrus | G01M 3/088 73/40 |
| 2,707,390 A | * | 5/1955 | Beretish | G01M 3/2876 73/46 |
| 3,043,129 A | * | 7/1962 | King | G01M 3/04 73/40 |

(Continued)

FOREIGN PATENT DOCUMENTS

| | | | | |
|---|---|---|---|---|
| FR | 2710747 A1 | * | 4/1995 | ............ G01M 3/226 |
| FR | 2971501 | | 8/2012 | |
| FR | 3037524 | | 12/2016 | |

OTHER PUBLICATIONS

ESPACENET Machine Translation of FR 2710747 A1 Which Originally Published on Apr. 7, 1995. (Year: 1995).*

(Continued)

*Primary Examiner* — David A. Rogers
(74) *Attorney, Agent, or Firm* — Dierker & Kavanaugh, P.C.

(57) ABSTRACT

An apparatus for automatic leak detection includes a fixture having a primary seal and a secondary seal. The fixture connects to a workpiece to enclose a test volume defined in the workpiece. The seals are to interface with the workpiece to at least partially enclose a buffer volume. An enclosure is to connect to the fixture to enclose a test portion of the workpiece to form a test chamber. The secondary seal separates the buffer volume from the test chamber. The test volume and the test chamber have a tracer gas pressure (Continued)

differential between them. A port in fluid communication with the buffer volume removes fixture leakage from the buffer volume. A detector detects the tracer gas in the test volume or the test chamber where the tracer gas pressure differential between the test volume and the test chamber urges workpiece leakage of the tracer gas to accumulate.

18 Claims, 13 Drawing Sheets

(56) References Cited

U.S. PATENT DOCUMENTS

| | | | | |
|---|---|---|---|---|
| 3,186,214 A * | 6/1965 | Roberts | ................ | G01M 3/226 73/40 |
| 3,572,096 A * | 3/1971 | Meyer | ................ | G01M 3/229 73/40.7 |
| 3,577,769 A * | 5/1971 | Roberts | ................ | G01M 3/229 73/40.7 |
| 3,672,207 A | 6/1972 | Cramp et al. | | |
| 3,762,212 A * | 10/1973 | Morley | ................ | G01M 3/202 376/250 |
| 3,864,960 A * | 2/1975 | Fletcher | ................ | G01M 3/002 73/46 |
| 4,274,007 A * | 6/1981 | Baatz | ................ | G21F 5/12 976/DIG. 349 |
| 4,420,970 A * | 12/1983 | Organi | ................ | G01M 3/2869 73/49.8 |
| 4,553,435 A * | 11/1985 | Goldfarb | ................ | G01M 3/225 73/49.3 |
| 4,791,806 A * | 12/1988 | Wade | ................ | G01M 3/205 73/40.7 |
| 4,813,268 A * | 3/1989 | Helvey | ................ | G01M 3/205 73/40.7 |
| 5,111,684 A * | 5/1992 | Stauffer | ................ | G01M 3/363 73/49.3 |
| 5,170,659 A * | 12/1992 | Kemp | ................ | F16L 23/167 137/557 |
| 5,172,583 A * | 12/1992 | Tallon | ................ | G01M 3/202 73/40.7 |
| 5,182,076 A * | 1/1993 | de Seroux | ................ | G21C 19/20 376/205 |
| 5,205,157 A * | 4/1993 | McDaniel | ................ | G01M 3/329 73/49.8 |
| 5,373,729 A * | 12/1994 | Seigeot | ................ | G01M 3/227 73/49.3 |
| 5,546,789 A * | 8/1996 | Balke | ................ | G01M 3/3281 73/40 |
| 6,000,422 A * | 12/1999 | Shigemoto | ................ | G01M 3/045 137/884 |
| 6,279,382 B1 * | 8/2001 | Yatagai | ................ | G01M 3/226 73/40.7 |
| 6,330,823 B1 * | 12/2001 | Raymond | ................ | G01M 3/3218 73/41.4 |
| 6,450,012 B1 * | 9/2002 | Mayer | ................ | G01M 3/227 73/49.3 |
| 6,608,490 B1 * | 8/2003 | Tombini | ................ | G01M 3/183 324/692 |
| 6,955,076 B1 * | 10/2005 | Widt | ................ | G01M 3/229 73/49.3 |
| 6,993,956 B2 * | 2/2006 | Bouten | ................ | G01N 15/082 73/40 |
| 7,448,256 B2 * | 11/2008 | Jenneus | ................ | G01M 3/226 73/49.2 |
| 8,261,596 B2 * | 9/2012 | Harrison | ................ | G01M 3/28 73/49.8 |
| 8,997,553 B2 | 4/2015 | McGregor | | |
| 9,395,263 B2 * | 7/2016 | Wang | ................ | G01M 3/34 |
| 9,732,997 B2 * | 8/2017 | Sishtla | ................ | F16L 23/18 |
| 11,105,704 B2 * | 8/2021 | Hogreve | ................ | G01M 3/227 |
| 2011/0132075 A1 | 6/2011 | Arvaneh | | |
| 2014/0151592 A1 * | 6/2014 | Ha | ................ | F16K 1/2261 73/40.7 |
| 2016/0103036 A1 * | 4/2016 | Wang | ................ | G01M 3/3272 73/40.7 |
| 2019/0301966 A1 | 10/2019 | Pillar | | |
| 2021/0025778 A1 * | 1/2021 | Ikegami | ................ | G01M 3/205 |
| 2022/0026303 A1 * | 1/2022 | Spanggaard | ................ | G01M 3/04 |

OTHER PUBLICATIONS

Crudgington, P.F., "Brush Seal Performance Evaluation", AIAA-98-3172, 1998, 8 pages.

Schroder, G., "New European Standard for the Selection of a Suitable Method for Leak Detection and Leak Tightness Testing", URL: https://www.itis-nl.com/wp-content/uploads/2016/07/EN1779-English.pdf, 2011, 12 pages.

Rottlander, H., et al. "Fundamentals of Leak Detection", Leybold GmbH, Cat. No. 199 79_VA.02, 2016, 49 pages.

Fuchs, A., et al., "Numerical Investigation on the Leakage of Brush Seals", Proceedings of Montreal 2018, Global Power and Propulsion Forum, May 7-9, 2018, 8 pages.

* cited by examiner

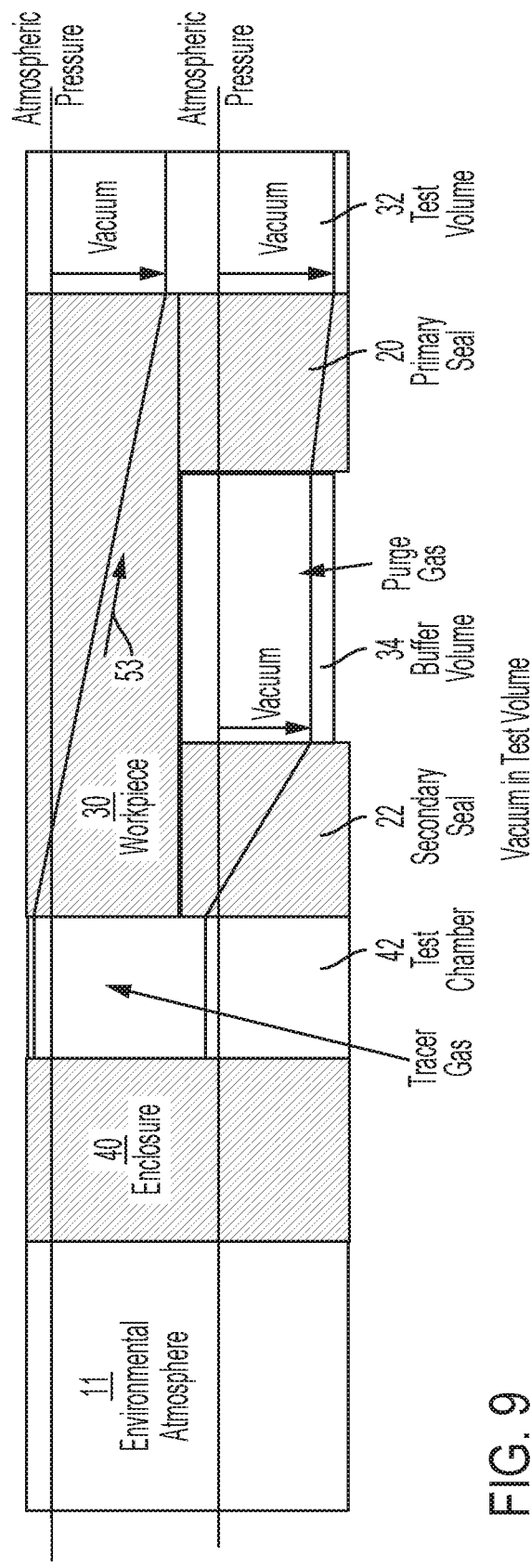
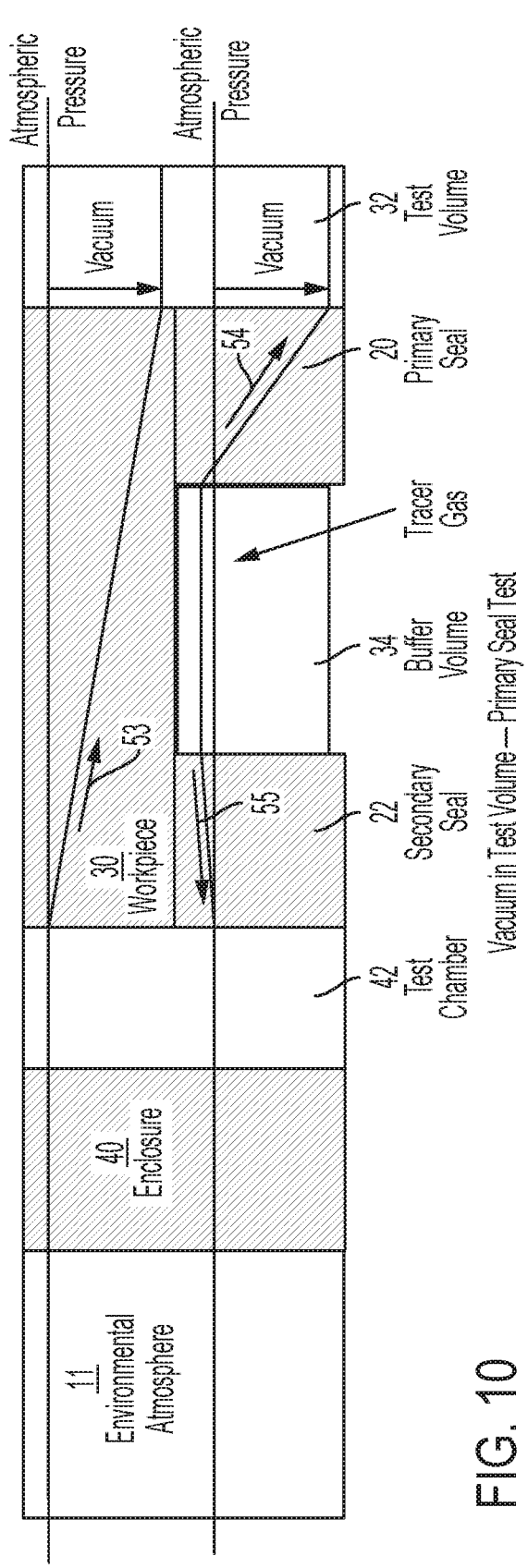
FIG. 9
FIG. 10

APPARATUS AND METHOD FOR AUTOMATIC LEAK DETECTION

TECHNICAL FIELD

The present disclosure relates generally to an apparatus and method for automatic leak detection.

BACKGROUND

During the manufacturing process of some devices, the devices are subjected to leak testing to identify defects. Leak testing may be done at any stage in the manufacturing of a part. If a leak or related defect can be identified early in a manufacturing process, value-added processes may be stopped on parts that are destined for rejection. In some cases, leakage at some particular rate may be identified as a defect. Parts may be required to be water tight, vapor tight, oil tight, or have some specification for maximum allowable leak.

There are existing methods for leak detection. For example, bubble testing can be used to detect leaks up to about $10^{-3}$ millibar*liter per second (mbar l/s). In an example, bubble testing may be used to identify and locate a leak in a tire. The inflated tire is dunked into a tub of water and a stream of air bubbles will flow from a leak. Characteristics of helium atoms are applied in some existing test methods to detect leaks through small defects that produce leaks less than $10^{-6}$ mbar l/s.

In some existing leak detection systems using existing methods, it can be difficult to distinguish a leak that would be classified as a defect in a part specimen from a leak that is caused by the test fixture or an interface between the test fixture and the part specimen to be tested. Bubbles may be produced by processes and mechanisms other than leaks. In the tire dunk test example, air bubbles may cling to the tire tread and be confused with a slow leak.

It may be desirable to identify casting defects such as cracks or porosity in a cast iron part, for example a brake master cylinder. Sealing surfaces of some master cylinders may be machined after casting to produce a smooth sealing interface for preventing brake fluid from leaking out of, and air from leaking into, the master cylinder during use. Leak testing in the as-cast condition may present a surface that is too rough for a leak testing device to reliably and repeatably seal against. Fixture leaks may be indistinguishable from defects in the specimen when certain existing test methods and equipment are used. Thus, sensitivity of existing test devices may be adjusted to prevent such false leaks from leading to a rejection of "good" parts. However, when less sensitive tests are used, some defective parts may slip through leak testing without being identified.

INTRODUCTION

A first aspect disclosed herein is an apparatus for automatic leak detection, comprising: a fixture having a primary seal and a secondary seal disposed thereon, wherein the fixture is to connect to a workpiece to enclose a test volume at least partially defined in the workpiece, wherein the primary seal and the secondary seal are to interface with the workpiece to at least partially enclose a buffer volume; an enclosure to connect to the fixture to enclose a test portion of the workpiece to form a test chamber, wherein the secondary seal is to separate the buffer volume from the test chamber; wherein the test volume and the test chamber are to have a tracer gas pressure differential established therebetween; a port in fluid communication with the buffer volume to remove at least a portion of a fixture leakage from the buffer volume; and a detector to detect an amount of the tracer gas in the test volume or the test chamber where the tracer gas pressure differential between the test volume and the test chamber urges workpiece leakage of the tracer gas to accumulate.

In an example of the first aspect, the buffer volume and the test chamber are to have a secondary seal pressure differential established therebetween, wherein the secondary seal pressure differential urges the tracer gas through a secondary seal leak, wherein detecting an amount of the tracer gas in the test chamber by the detector is indicative of the secondary seal leak.

In an example of the first aspect, the primary seal includes a first lip of a double seal, and the secondary seal includes a second lip of the double seal, wherein a groove is defined between the first lip and the second lip, wherein the groove defines at least a portion of the buffer volume. In one example, the buffer volume is bounded by the first lip, the second lip and the workpiece.

In an example of the first aspect, the buffer volume is bounded by the primary seal, the secondary seal, the workpiece and the fixture. In one example, the primary seal is attached to the secondary seal by at least a partial web.

In an example of the first aspect, the tracer gas pressure differential is to be established by causing the tracer gas pressure to be higher in the test volume than in the test chamber. In one example, the tracer gas pressure differential is to be established by transferring tracer gas into the test volume by opening a tracer-to-test volume valve connected to a source of the tracer gas.

In an example of the first aspect, the apparatus further comprises a buffer volume inlet in fluid connection with the buffer volume for flowing a purge gas through the buffer volume and out through the port to remove the at least a portion of the fixture leakage from the buffer volume by flushing at least a portion of the fixture leakage out of the buffer volume.

In an example of the first aspect, the apparatus further comprises a pump in fluid communication with the buffer volume for removing the at least a portion of the fixture leakage from the buffer volume by at least partially evacuating the buffer volume via the pump.

In an example of the first aspect, the test chamber comprises at least two fluidly separate subchambers, wherein the detector is in branched fluid communication with the at least two fluidly separate subchambers via fluid communication branches, wherein at least one valve opens and closes the fluid communication branches to temporally separate a detector signal associated with each of the at least two fluidly separate subchambers.

In an example of the first aspect, the apparatus further comprises a differential pressure sensor in fluid communication with the buffer volume and the test chamber for determining a differential pressure between the buffer volume and the test chamber.

In an example of the first aspect, the tracer gas includes helium gas. In an example of the first aspect, the tracer gas includes hydrogen gas. In an example of the first aspect, the tracer gas includes forming gas. In an example of the first aspect, the detector includes a mass spectrometer. In an example of the first aspect, the detector includes an electronic hydrogen detector.

In an example of the first aspect, the apparatus further comprises an enclosure seal disposed between the enclosure and the fixture to form an enclosure-fixture joint. In one example, the enclosure-fixture joint has an enclosure-fixture joint leak rate that is smaller than a flow rate of the tracer gas into the test chamber. In one example, the enclosure seal includes a brush seal.

It is to be understood that any features of the apparatus for automatic leak detection disclosed herein may be combined together in any desirable manner and/or configuration.

A second aspect disclosed herein is a method for automatic leak detection, comprising: connecting a workpiece to a fixture thereby enclosing a test volume, wherein a primary seal and a secondary seal are each disposed between the fixture and the workpiece to enclose a buffer volume; connecting an enclosure to the fixture to enclose a test portion of the workpiece to form a test chamber, wherein the secondary seal separates the buffer volume from the test chamber; establishing a tracer gas pressure differential between the test volume and the test chamber; removing at least a portion of a fixture leakage from the buffer volume; and detecting an amount of the tracer gas in the test volume or the test chamber where the tracer gas pressure differential between the test volume and the test chamber urges workpiece leakage of the tracer gas to accumulate.

In an example of the second aspect, the method further comprises: using the tracer gas, establishing a secondary seal pressure differential between the buffer volume and the test chamber; and detecting an amount of the tracer gas in the test chamber to detect a leak at the secondary seal.

In an example of the second aspect, the primary seal includes a first lip of a double seal, and the secondary seal includes a second lip of the double seal, wherein a groove is defined between the first lip and the second lip, wherein the groove defines at least a portion of the buffer volume. In one example, the buffer volume is bounded by the first lip, the second lip and the workpiece.

In an example of the second aspect, the buffer volume is bounded by the primary seal, the secondary seal, the workpiece and the fixture. In one example, the primary seal is attached to the secondary seal by at least a partial web.

In an example of the second aspect, the establishing the tracer gas pressure differential includes causing the tracer gas pressure to be higher in the test volume than in the test chamber. In one example, the establishing the tracer gas pressure differential includes transferring tracer gas into the test volume by opening a tracer-to-test volume valve connected to a source of the tracer gas.

In an example of the second aspect, the removing at least a portion of the fixture leakage from the buffer volume includes flowing a purge gas through the buffer volume to flush at least a portion of the fixture leakage out of the buffer volume. In one example, the removing at least a portion of the fixture leakage from the buffer volume includes at least partially evacuating the buffer volume via a pump.

In an example of the second aspect, tracer gas includes helium gas. In an example of the second aspect, the tracer gas includes hydrogen gas. In an example of the second aspect, the tracer gas includes forming gas.

In an example of the second aspect, detecting an amount of the tracer gas involves using a mass spectrometer. In an example of the second aspect, detecting an amount of the tracer gas involves using an electronic hydrogen detector.

In an example of the second aspect, an enclosure seal is disposed between the enclosure and the fixture forming an enclosure-fixture joint. In one example, the enclosure-fixture joint has an enclosure-fixture joint leak rate that is smaller than the flow rate of the tracer gas into the test chamber. In one example, the enclosure seal includes a brush seal.

It is to be understood that any features of this method may be combined together in any desirable manner. Moreover, it is to be understood that any combination of features of this method and/or of the apparatus for automatic leak detection may be used together, and/or combined with any of the examples disclosed herein.

SUMMARY

An apparatus for automatic leak detection includes a fixture having a primary seal and a secondary seal. The fixture connects to a workpiece to enclose a test volume defined in the workpiece. The seals are to interface with the workpiece to at least partially enclose a buffer volume. An enclosure is to connect to the fixture to enclose a test portion of the workpiece to form a test chamber. The secondary seal separates the buffer volume from the test chamber. The test volume and the test chamber have a tracer gas pressure differential between them. A port in fluid communication with the buffer volume removes fixture leakage from the buffer volume. A detector detects the tracer gas in the test volume or the test chamber where the tracer gas pressure differential between the test volume and the test chamber urges workpiece leakage of the tracer gas to accumulate.

BRIEF DESCRIPTION OF THE DRAWINGS

Features of examples of the present disclosure will become apparent by reference to the following detailed description and drawings, in which like reference numerals correspond to the same or similar, though perhaps not identical, components. For the sake of brevity, reference numerals or features having a previously described function may or may not be described in connection with other drawings in which they appear.

FIG. 9 is a diagram depicting an example of relative pressures in a leak test apparatus as disclosed herein;

FIG. 10 is a diagram depicting an example of relative pressures in a leak test apparatus as disclosed herein.

DETAILED DESCRIPTION

Figure 1:
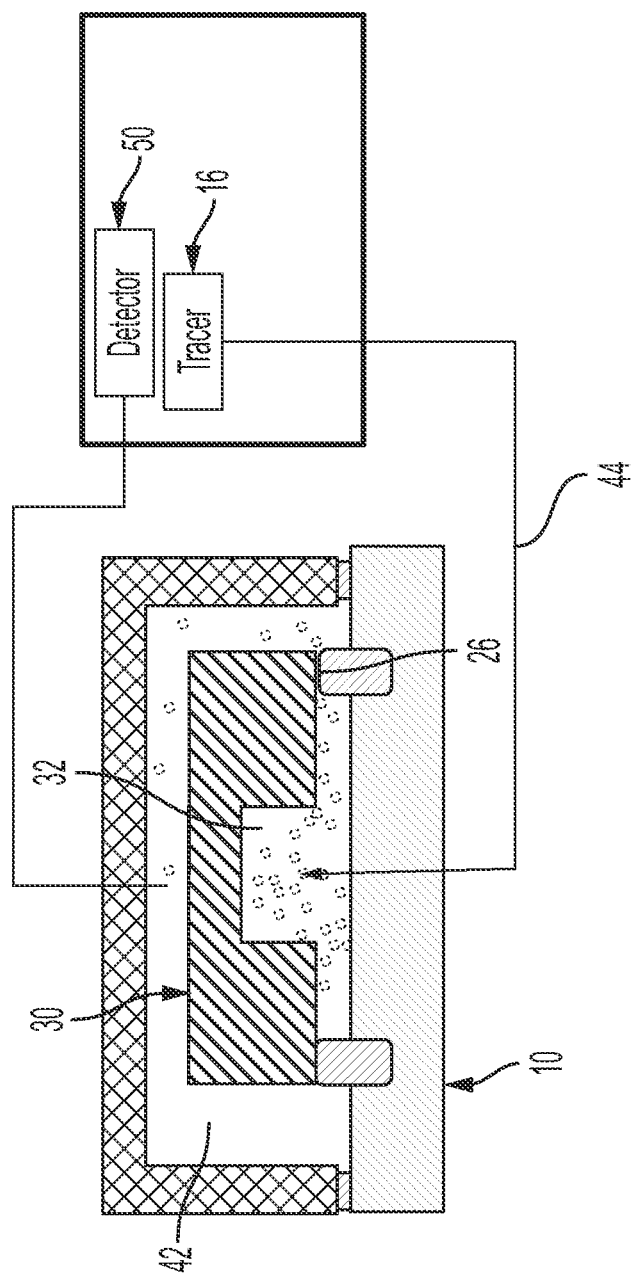
FIG. 1 is a semi-schematic diagram of a workpiece on a leak test fixture.

FIG. 1 is a semi-schematic diagram of a workpiece 30 on a leak test fixture 10. A tracer gas is injected into a test volume 32 If a leaking passageway or mechanism (not shown in FIG. 1) is present in the workpiece 30, the tracer gas will flow through the leaking passageway or mechanism into the test chamber 42. If the detector 50 determines that a certain amount of the tracer gas is present in the test chamber 42, the detector 50 indicates that the workpiece 30 has a leaking passageway or mechanism. The leak test fixture 10 depicted in FIG. 1 includes a seal at an interface to the workpiece 30. FIG. 1 depicts a fixture leak at the interface between the seal and the workpiece 30. The tracer gas that flows through the leak is labeled as fixture leakage 14. The fixture leakage 14 is potentially indistinguishable by the detector 50 from tracer gas due to a leaking passageway or mechanism in the workpiece 30. As such, there is a possibility of the detector 50 of an existing leak detection system and method indicating that a leaking passageway or mechanism exists in the workpiece 30 when the tracer gas that is admitted into the test chamber 42 is actually fixture leakage 14—a false positive result. If the workpiece 30 has a leaking passageway or mechanism at the same time as a fixture leakage 14, the tracer gas can mix in the test chamber 42 and confound the detector 50—potentially causing the detector 50 to indicate that a certain threshold of leakage has been detected. To compensate for such a condition, some existing leak detection systems may set a threshold for indicating a leak high enough that fixture leakage 14 does not cause false positive results. Such a compensation scheme may decrease the sensitivity of the existing leak detection system and inhibit the detection of small leaks. In the drawings of the present disclosure, flowpaths 44 are depicted by a line. It is to be understood that such flowpaths 44 may represent, e.g., tubing, a cannula, or a channel defined in a part (e.g. a wormtrail manifold). Connectors, gaskets, or seals may be used to prevent leaks at flowpath connections.

Figure 2A:
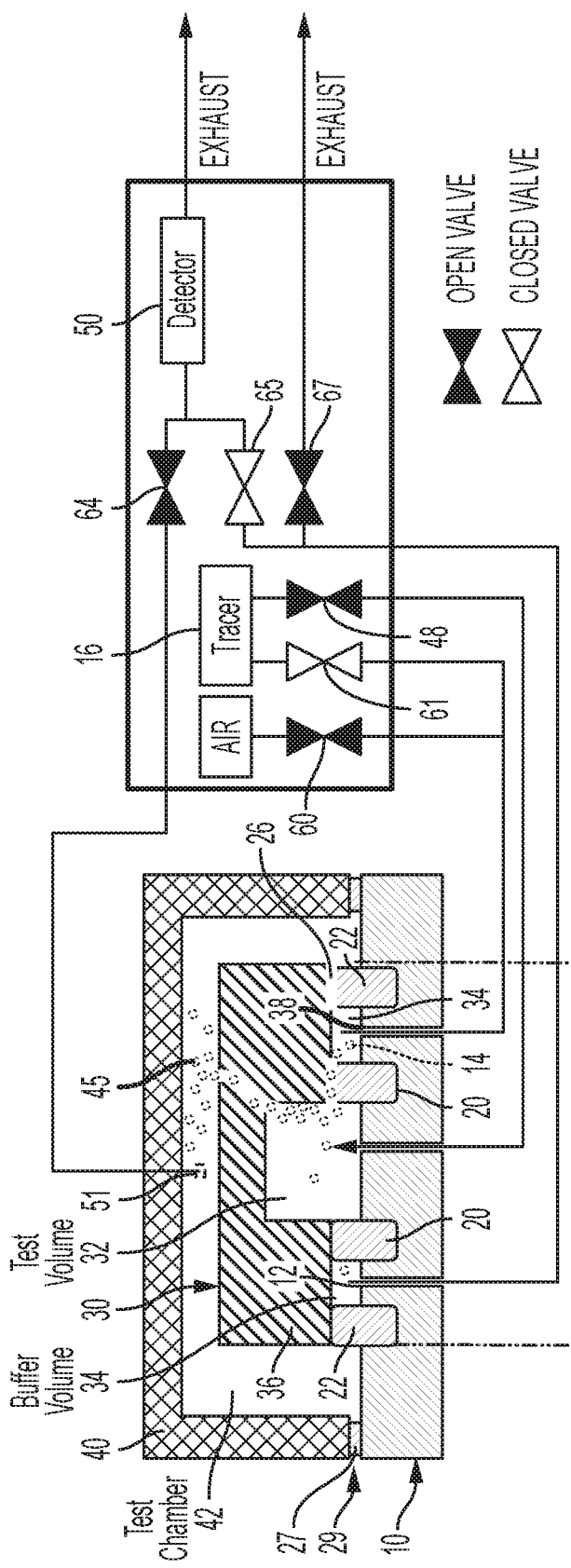
FIG. 2A is a semi-schematic diagram of an example of a leak test apparatus according to the present disclosure.
Figure 2A:
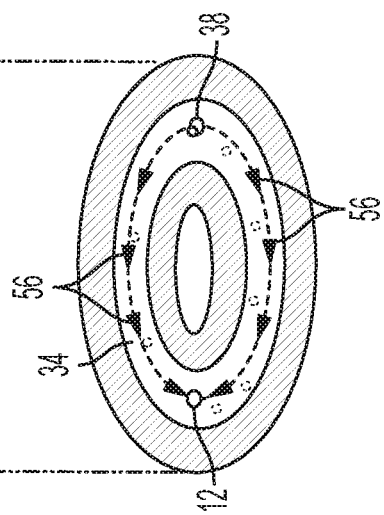

FIG. 2A is a semi-schematic diagram of an example of an apparatus for automatic leak detection according to the present disclosure. As depicted in FIG. 2A, in examples of the present disclosure, an apparatus for automatic leak detection includes a fixture 10 having a primary seal 20 and a secondary seal 22 disposed thereon. The fixture 10 is to connect to a workpiece 30 to enclose a test volume 32 at least partially defined in the workpiece 30. The primary seal 20 and the secondary seal 22 are to interface with the workpiece 30 to at least partially enclose a buffer volume 34. In examples, the apparatus for automatic leak detection includes an enclosure 40 to connect to the fixture 10 to enclose a test portion 36 of the workpiece 30 to form a test chamber 42. The secondary seal 22 is to separate the buffer volume 34 from the test chamber 42.

The test volume 32 and the test chamber 42 are to have a tracer gas pressure differential established therebetween. As disclosed herein, the tracer gas may include any detectable gas or gas mixture. In examples, the tracer gas is normally not present, or present in small amounts in air. In an example, the tracer gas may include helium (He) gas. In an example, the tracer gas may include 10% He, 90% Nitrogen ($N_2$) gas. In another example, the tracer gas may include 40% He and 60% $N_2$. Helium is normally present in air at about 0.0005 percent by volume. It should be noted that the background amount of the tracer gas may be locally higher in an environment where the tracer gas is used for continuous testing. In another example, the tracer gas may include hydrogen gas. In yet another example, the tracer gas may include forming gas. As used herein, "forming gas" means a mixture of hydrogen gas ($H_2$) and nitrogen gas ($N_2$). In examples, the forming gas may have a mixture of less than 5% $H_2$ in $N_2$ by volume. In another example, the tracer gas may include sulfur hexafluoride ($SF_6$). In an example, the tracer gas may include a detectable concentration of propane gas ($C_3H_8$). In an example, the tracer gas may include a detectable concentration of methane gas ($CH_4$).

In examples, the detector 50 may include any electronic device to detect the presence and/or amount of the tracer gas or a constituent of the tracer gas. In an example, the detector 50 includes a mass spectrometer 46. In another example, the detector 50 includes an electronic hydrogen detector 51. An example of an electronic hydrogen detector 51 is an SGAS701 Trace Hydrogen Gas Sensor, available from Integrated Device Technology, Inc. The SGAS701 is a solid-state chemiresistor sensor designed to detect hydrogen in air. In an example, the detector 50 may include a Volatile Organic Compound (VOC) sensor. In an example, the detector 50 may include a Metal-Oxide-Semiconductor (MOS)-based gas sensor. An example of an MOS-based gas sensor is a TGS821 Hydrogen Sensor, available from Figaro. In an example, the detector 50 may include a catalytic VOC sensor. An example of a catalytic sensor is a TGS6812-D00 Hydrogen/Methane/LPG Sensor, available from Figaro. In an example, the detector 50 may include an electrochemical gas sensor. An example of an electrochemical gas sensor is a FECS50-100 Hydrogen Sulfide Sensor, available from Figaro. It is to be understood that certain detectors 50, for example some mass spectrometers 46, are compatible with operation in a hard vacuum. Other detectors 50 are more suitable for operation near atmospheric pressure. It is to be understood that any combination of features of the method and/or of the apparatus for automatic leak detection may be used together, and/or combined with any of the examples disclosed herein. As such, a detector 50 that is suitable for the operating conditions, including pressure range, is selected.

Examples of the apparatus for automatic leak detection disclosed herein may include an enclosure seal 27 disposed between the enclosure 40 and the fixture 10 to form an enclosure-fixture joint 29 as depicted in FIG. 2A. In examples, the enclosure-fixture joint 29 may have an enclosure-fixture joint 29 leak rate that is smaller than the flow rate of the tracer gas into the test chamber 42. The enclosure seal 27 may use any suitable seal technology. In an example, the enclosure seal 27 may include a brush seal. As used herein, a brush seal means a contact seal that includes an array or bundle of filaments that span a gap between two surfaces. The filaments are arranged to inhibit or prevent a flow of fluid, dust, or particles through the gap. The filaments may be made of an elastomer, plastic, hair, metal or combinations thereof.

Figure 6:
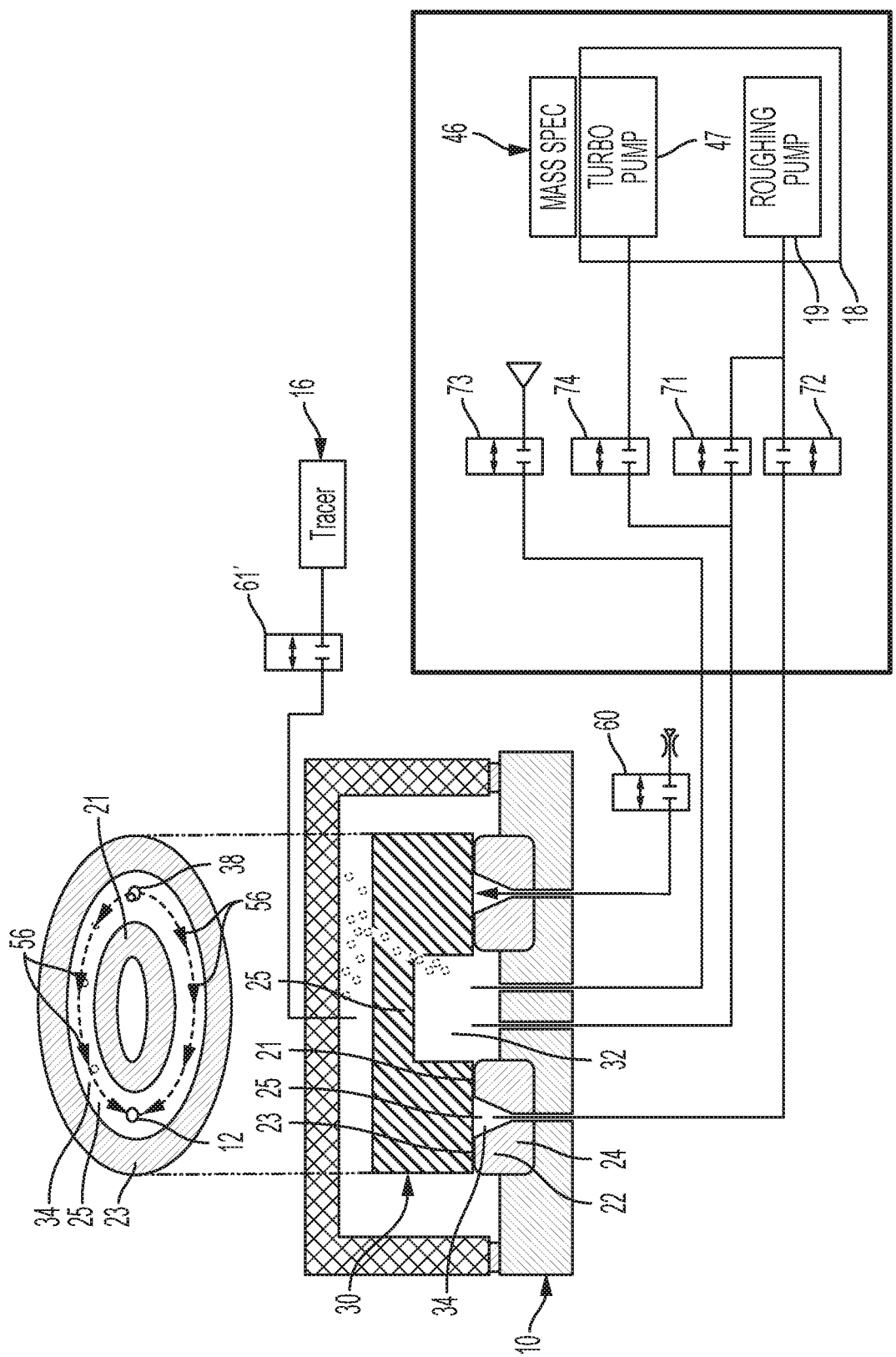
FIG. 6 is a semi-schematic diagram of another example of a leak test apparatus according to the present disclosure.
Figure 7A:
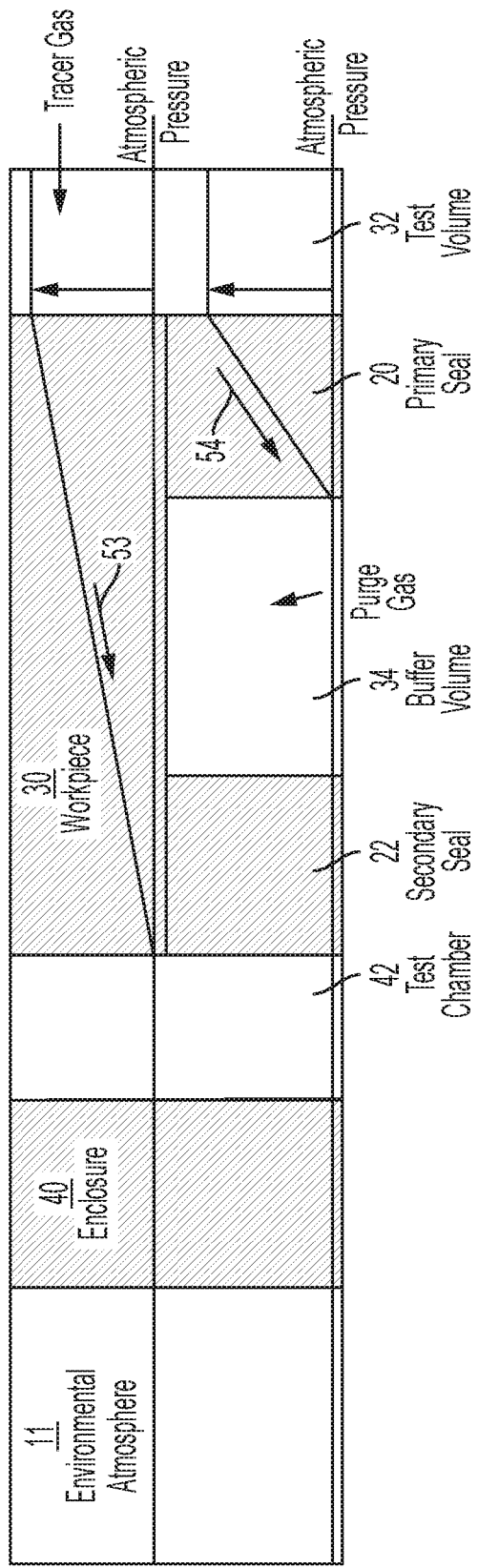
FIG. 7A is a diagram depicting an example of relative pressures in a leak test apparatus as disclosed herein.

In an example as depicted in FIG. 2A and FIG. 7A, the tracer gas pressure differential is to be established by causing the tracer gas pressure to be higher in the test volume 32 than in the test chamber 42. For example, the tracer gas pressure may be higher in than atmospheric pressure in the test volume 32 and at atmospheric pressure in the test chamber 42. In another example (See FIG. 2C), the test chamber 42 may be evacuated by a vacuum pump 18, and the tracer gas may be injected into the test volume 32. In examples in which the pressure in the test volume 32 is higher than the pressure in the test chamber 42, the tracer gas will tend to flow from the test volume 32 to the test chamber 42 if a path is available. In examples, the tracer gas pressure differential may be established by transferring tracer gas into the test volume 32 by opening a tracer-to-test volume valve 48 connected to a source 16 of the tracer gas. In FIG. 2A, the tracer-to-test volume valve 48 is connected to the source 16 of the tracer gas; and the tracer-to-test volume valve 48 is opened to transfer the tracer gas from the source 16 to the test volume 32. The normal atmosphere present in the test volume 32 may be removed or partially removed (e.g. by a vacuum pump 18 as shown in FIG. 6) prior to the transfer of the tracer gas into the test volume 32 to decrease dilution and increase the concentration of the tracer gas.

In an example, as depicted in FIG. 2A, the apparatus for automatic leak detection may include a buffer volume inlet 38 in fluid connection with the buffer volume 34 for flowing a purge gas through the buffer volume 34 and out through the port 12 to remove the at least a portion of the fixture leakage 14 from the buffer volume 34 by flushing at least a portion of the fixture leakage 14 out of the buffer volume 34. The flow direction of a bulk flow of the purge gas is represented by flow arrows 56 in FIGS. 2A-6.

Without being held bound to any theory, it is believed that several modes of transport of the gas molecules are effective in the present disclosure. Diffusion is net movement of particles of matter (for example, atom, ions, molecules) from a region of higher concentration to a region of lower concentration. Diffusion is driven by a gradient in concentration. Diffusion depends on random particle motion, and causes the tracer gas to mix in a volume without requiring directed bulk motion. Diffusion is the gradual movement or dispersion of concentration within a body, due to a concentration gradient, with no net movement of matter. "Bulk flow" is a movement or flow of an entire body due to a pressure gradient. Water coming out of a faucet is an example of bulk flow. Effusion is the process in which a gas escapes from a container through a hole of diameter considerably smaller than the mean free path of the molecules. The escape of the gas through the hole is due to the pressure difference between the container and the exterior. Under these conditions, all of the molecules which arrive at the hole continue and pass through the hole, since collisions between molecules in the region of the hole are negligible. In the Figs. of the present disclosure, the size of the leaks are depicted as approximately the same as the size of the molecules—this is a drawing convenience, and not a limitation. As such, although the tracer gas may move through a defect in the workpiece 30 by effusion, the defects may be much larger than the mean free path of the tracer gas, and the tracer gas may also move and mix by diffusion and bulk flow. After the tracer gas enters the buffer volume 34, eventually, in an absence of bulk flow, the concentration of tracer gas throughout the buffer volume 34 will equalize. In such a situation, the tracer gas will tend to flow through fixture leaks by diffusion even if there is no pressure gradient. However, if a sufficient purging bulk flow is present, the concentration of the tracer gas in the buffer volume 34 is negligibly low, preventing significant flow of tracer gas through the fixture leak by any mechanism (i.e. bulk flow, diffusion, or effusion).

Still referring to FIG. 2A, in examples, the apparatus for automatic leak detection includes a port 12 in fluid communication with the buffer volume 34 to remove at least a portion of a fixture leakage 14 from the buffer volume 34. The apparatus for automatic leak detection includes a detector 50 to detect an amount of the tracer gas in the test volume 32 or the test chamber 42 where the tracer gas pressure differential between the test volume 32 and the test chamber 42 urges workpiece leakage 45 of the tracer gas to accumulate. For example, if the pressure in the test volume 32 is higher than the pressure in the test chamber 42, workpiece leakage 45 of the tracer gas will tend to accumulate in the test chamber 42. On the other hand, if the pressure in the test chamber 42 is higher than the pressure in the test volume 32, the workpiece leakage 45 of the tracer gas will tend to accumulate in the test volume 32.

Figure 2B:
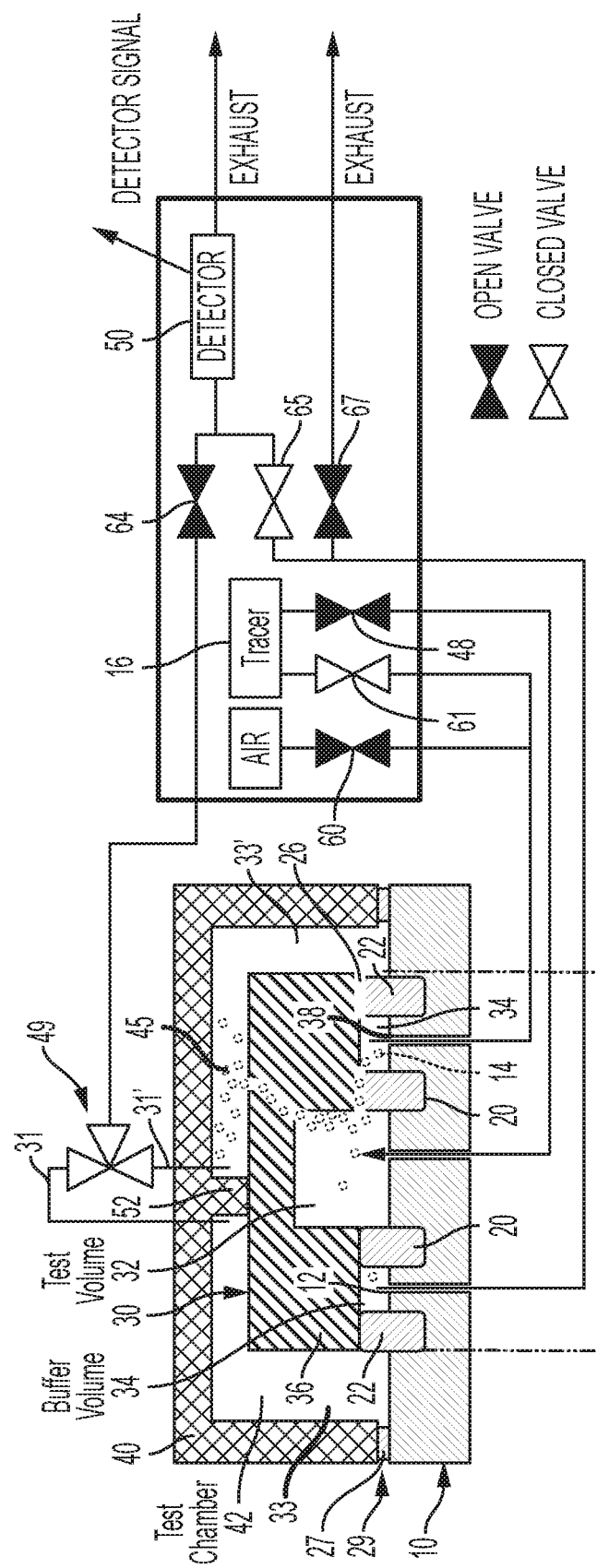
FIG. 2B is a semi-schematic diagram of an example of a leak test apparatus according to the present disclosure.
Figure 2B:
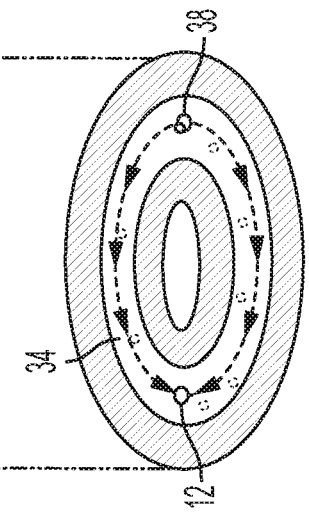

In an example as depicted in FIG. 2B, the test chamber comprises at least two fluidly separate subchambers 33, 33'. The detector 50 is in branched fluid communication with the at least two fluidly separate subchambers 33, 33' via fluid communication branches 31, 31'. At least one valve 49 opens and closes the fluid communication branches 31, 31' to temporally separate a detector signal associated with each of the at least two fluidly separate subchambers 33, 33'. In an example, the at least one valve 49 may be a 3-way valve as shown in FIG. 2B, however, any combination of valves that connects the fluid communication branches at non-overlapping time intervals is contemplated herein. In FIG. 2B, the at least two fluidly separate subchambers 33, 33' are shown having a shared wall 52. In other examples, the separate subchambers may be completely separate, having no shared walls. In yet other examples, there may be a plurality of detectors that operates in parallel. Thus, the apparatus is able to determine a location for each detector signal at the same time.

Figure 2C:
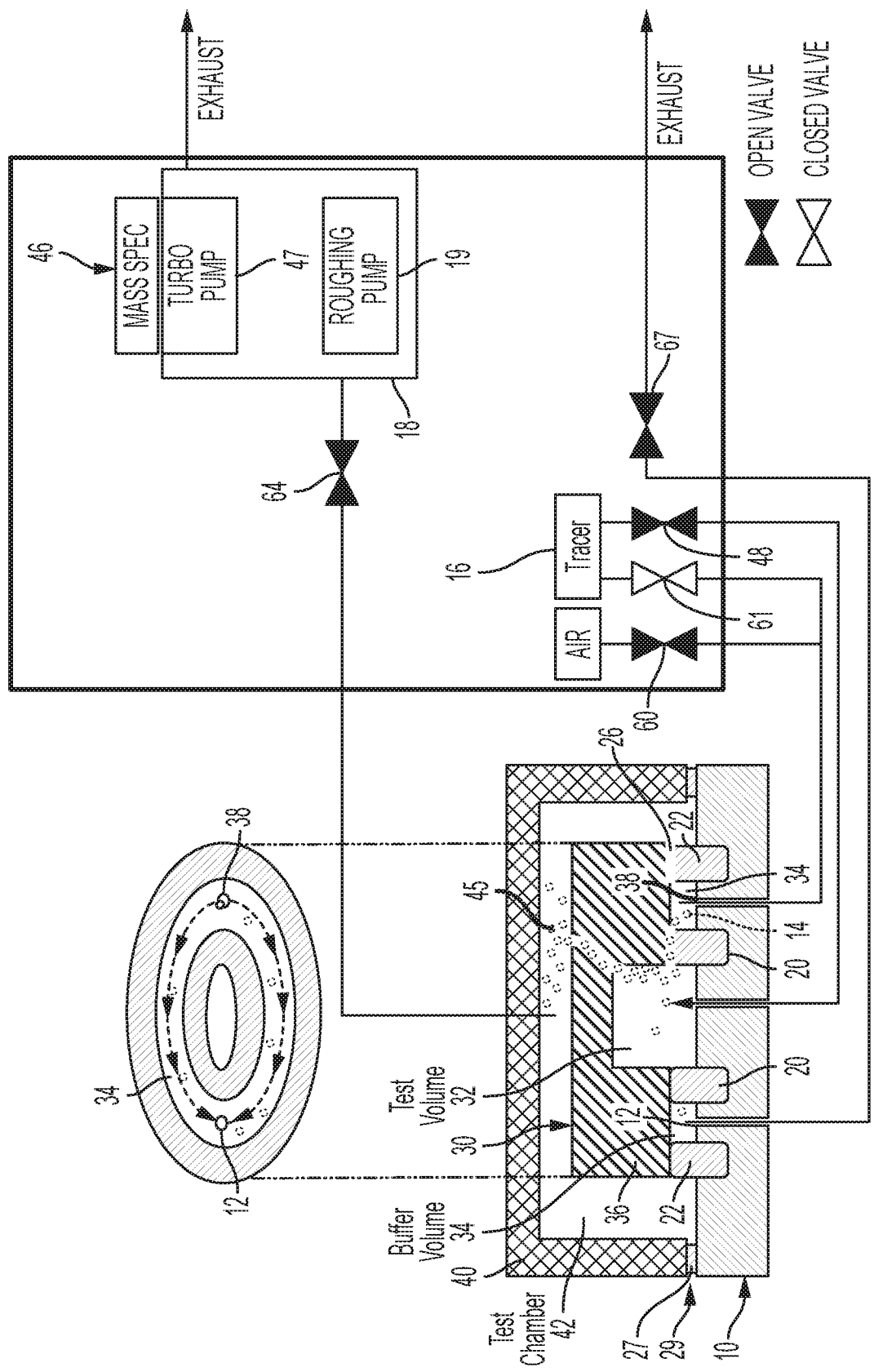
FIG. 2C is a semi-schematic diagram of an example of a leak test apparatus according to the present disclosure.
Figure 7B:
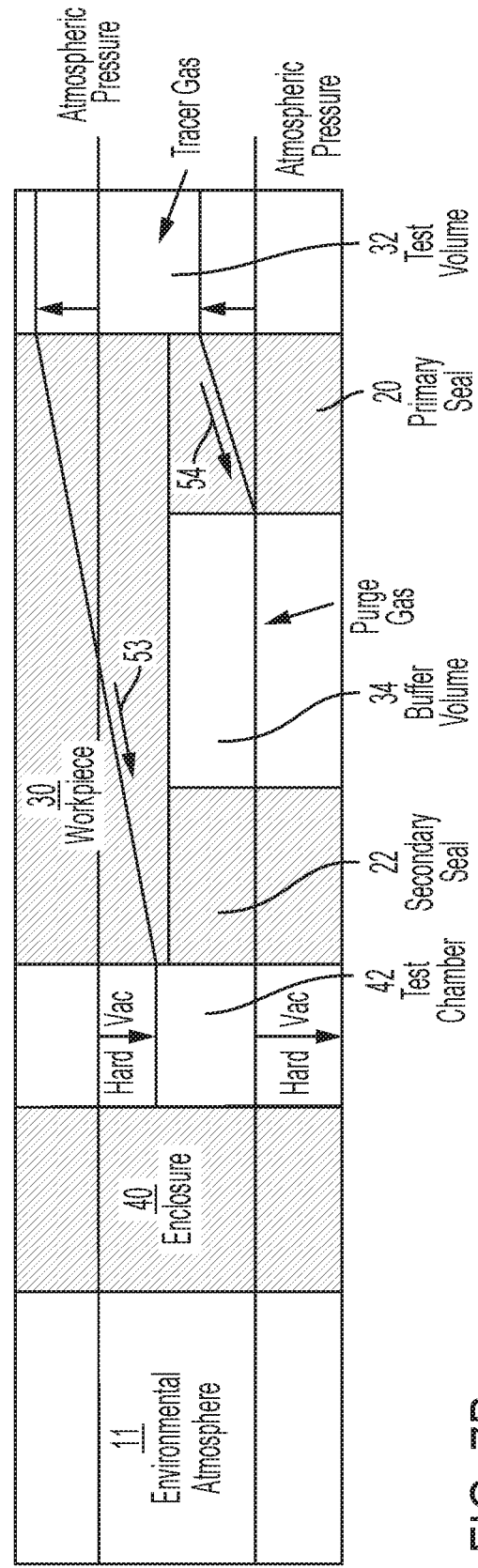
FIG. 7B is a diagram depicting an example of relative pressures in a leak test apparatus as disclosed herein.

In an example as depicted in FIG. 2C and FIG. 7B, the tracer gas pressure differential is to be established by causing the tracer gas pressure to be higher in the test volume 32 than in the test chamber 42. For example, the test chamber 42 may be evacuated by a vacuum pump 18, and the tracer gas may be injected into the test volume 32. In examples, the vacuum pump 18 may create any level of vacuum up to an ultra-high vacuum. In examples, the vacuum pump 18 may create a hard vacuum in the test chamber 42. In examples, the vacuum pump 18 may create a rough vacuum in the test chamber 42. In examples in which the pressure in the test volume 32 is higher than the pressure in the test chamber 42, the tracer gas will tend to flow from the test volume 32 to the test chamber 42 if a path is available. In examples, the tracer gas may be transferred into the test volume 32 by opening a tracer-to-test volume valve 48 connected to a source 16 of the tracer gas and by evacuating the test chamber 42 with a vacuum pump 18. In FIG. 2C, the tracer-to-test volume valve 48 is connected to the source 16 of the tracer gas; and the tracer-to-test volume valve 48 is opened to transfer the tracer gas from the source 16 to the test volume 32.

Figure 2D:
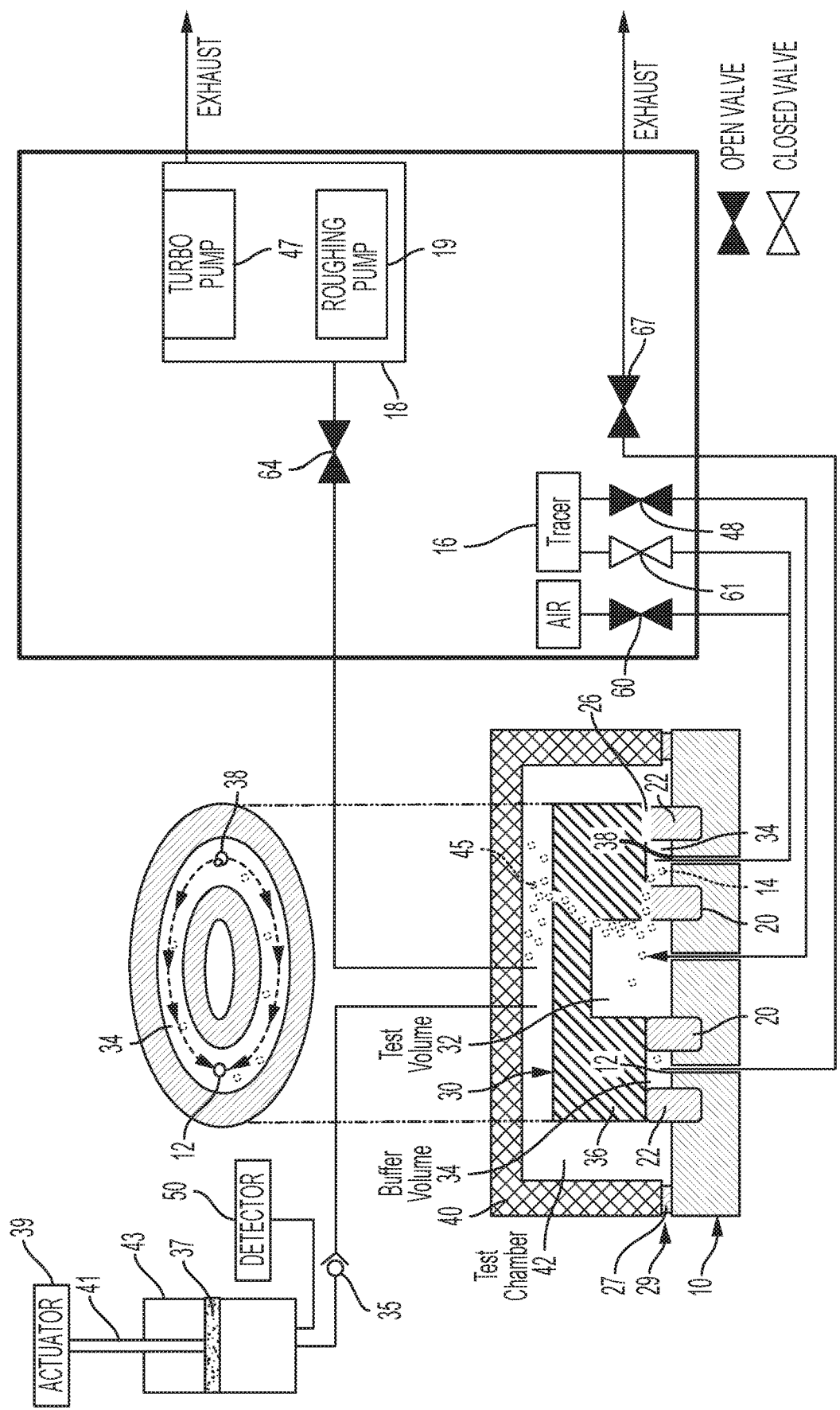
FIG. 2D is a semi-schematic diagram of an example of a leak test apparatus according to the present disclosure.

In an example as depicted in FIG. 2D and FIG. 7B, the tracer gas pressure differential is to be established by causing the tracer gas pressure to be higher in the test volume 32 than in the test chamber 42. For example, the test chamber 42 may be evacuated by a vacuum pump 18, and the tracer gas may be injected into the test volume 32. In the example depicted in FIG. 2D, the vacuum pump 18 may create a hard vacuum in the test chamber 42. As stated herein above, some detectors 50 may be more suitable for operation with samples that are more near atmospheric pressure than a hard vacuum. In the example depicted in FIG. 2D, the test chamber 42 is at hard vacuum and the workpiece leakage 45 accumulates in the test chamber 42. A cylinder 43 has a piston 37 translatable within the cylinder 43 to draw a sample from the test chamber 42. In FIG. 2D, an actuator 39 is connected to the piston 37 via a piston rod 41 to actuate the piston 37. It is to be understood that any suitable actuator 39 that can move the piston 37 is contemplated herein. For example, the actuator 39 may be another piston, a rotary motor connected via a crankshaft, a linear actuator, a screw drive, a hydraulic actuator or a pneumatic actuator. A check valve 35, or other valves and conduits may be included to direct and contain fluid flow. For example a valve (not shown) may admit clean air for flushing the sample from the detector 50 after a test. After the piston 37 has withdrawn a sample into the cylinder, the piston 37 may compress the sample, thereby concentrating workpiece leakage 45 and increasing the sample pressure to a pressure that is compatible with the detector 50. It is to be understood that a rearrangement of valves could be used to decrease the pressure of a sample withdrawn at a higher pressure, for example to be compatible with a mass spectrometer that operates with samples at hard vacuum.

Figure 3:
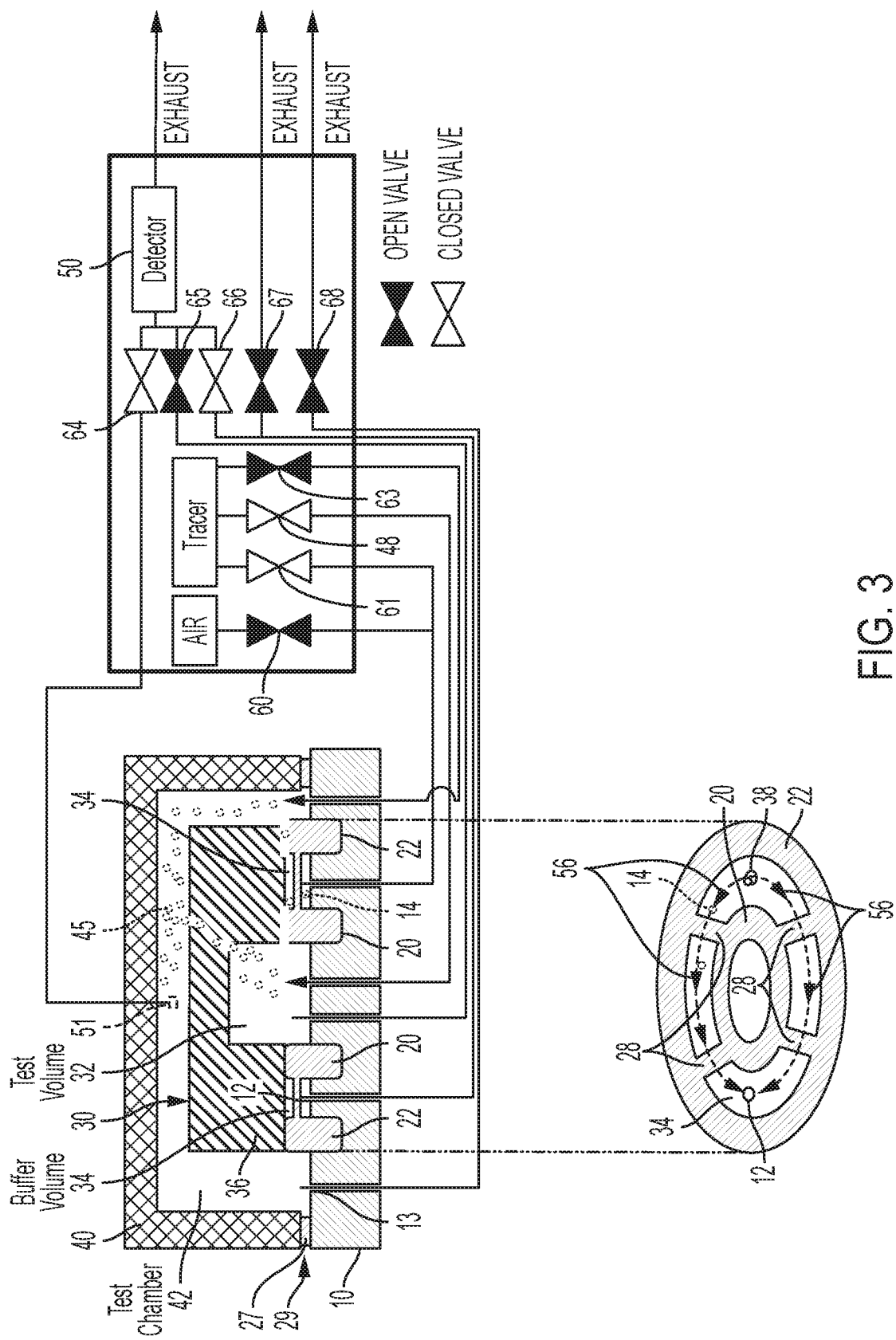
FIG. 3 is a semi-schematic diagram of another example of a leak test apparatus according to the present disclosure.

FIG. 3 is a semi-schematic diagram of another example of a leak test apparatus according to the present disclosure. The example depicted in FIG. 3 can be configured to operate in the same modes as the example in FIG. 2A, however, because of additional valves and flow paths, the example depicted in FIG. 3 may be configured to establish the tracer gas pressure differential between the test chamber and the test volume by opening a tracer-to-test chamber valve 63 and injecting tracer gas in the test chamber 42. In some examples, the test chamber 42 may be pressurizable; in other examples, the test chamber 42 may not be pressurizable. In examples where the test chamber 42 is not to be pressurized, a test chamber exhaust port 13 may be connected to a test chamber exhaust valve 68 to exhaust gas from the test chamber 42 and equalize pressure in the test chamber 42 with the environmental atmosphere 11 when the tracer gas is injected into the test chamber 42. Exhausting outside of the test area may reduce a potential for exhaust gases to interfere with test results. Examples may include an enclosure seal 27 disposed between the enclosure 40 and the fixture 10 to form an enclosure-fixture joint 29 as depicted in FIG. 3. In examples, the enclosure-fixture joint 29 may have an enclosure-fixture joint 29 leak rate that is smaller than the flow rate of the tracer gas into the test chamber 42. When the partial pressure of the tracer gas is higher in the test chamber 42 than the test volume 32, the tracer gas pressure differential (e.g. the tracer gas partial pressure differential) between the test volume and the test chamber urges workpiece leakage of the tracer gas to accumulate in the test volume 32. The flow of the tracer gas may be driven by a pressure gradient, a concentration gradient, or a combination of both a pressure and concentration gradient.

FIG. 3 depicts fixture leakage 14 being flushed out of the buffer volume 34 by opening air admittance valve 60 to flow air or nitrogen gas through the buffer volume inlet 38. Fixture leakage is carried along with the bulk flow of air out of the buffer volume 34 through the port 12 and is exhausted via open exhaust valve 67. In examples, the primary seal 20 may be attached to the secondary seal 22 by at least a partial web 28. In FIG. 3, the partial web 28 is a plurality of struts of the same material that composes the primary seal 20 and the secondary seal 22. In an example, the partial web 28 may be comolded with the primary seal 20 and the secondary seal 22. In another example, the partial web 28 may be overmolded over the primary seal 20 and the secondary seal 22. In still other examples, the web may be made from a different material from the primary seal 20 and the secondary seal 22. For example, a metal or plastic skeleton may be overmolded by an elastomer to form the primary seal 20 and the secondary seal 22 with metal spokes extending between the primary seal 20 and the secondary seal 22.

FIG. 3 depicts a flow of gas from the test volume 32 through the second detector valve 65 to the detector 50. In other examples, a detector 51 may be mounted in the test volume 32 and an electronic, photonic, acoustic or radio signal transmitted therefrom. Similarly, a flow of gas may be transmitted from the test chamber 42 through the first detector valve 64 to the detector 50. A flow of gas may be transmitted from the buffer volume 34 through the third detector valve 66 to the detector 50. In other examples, the detector 51 may be mounted in the test chamber 42 and an electronic, photonic, acoustic or radio signal transmitted therefrom.

Figure 4:
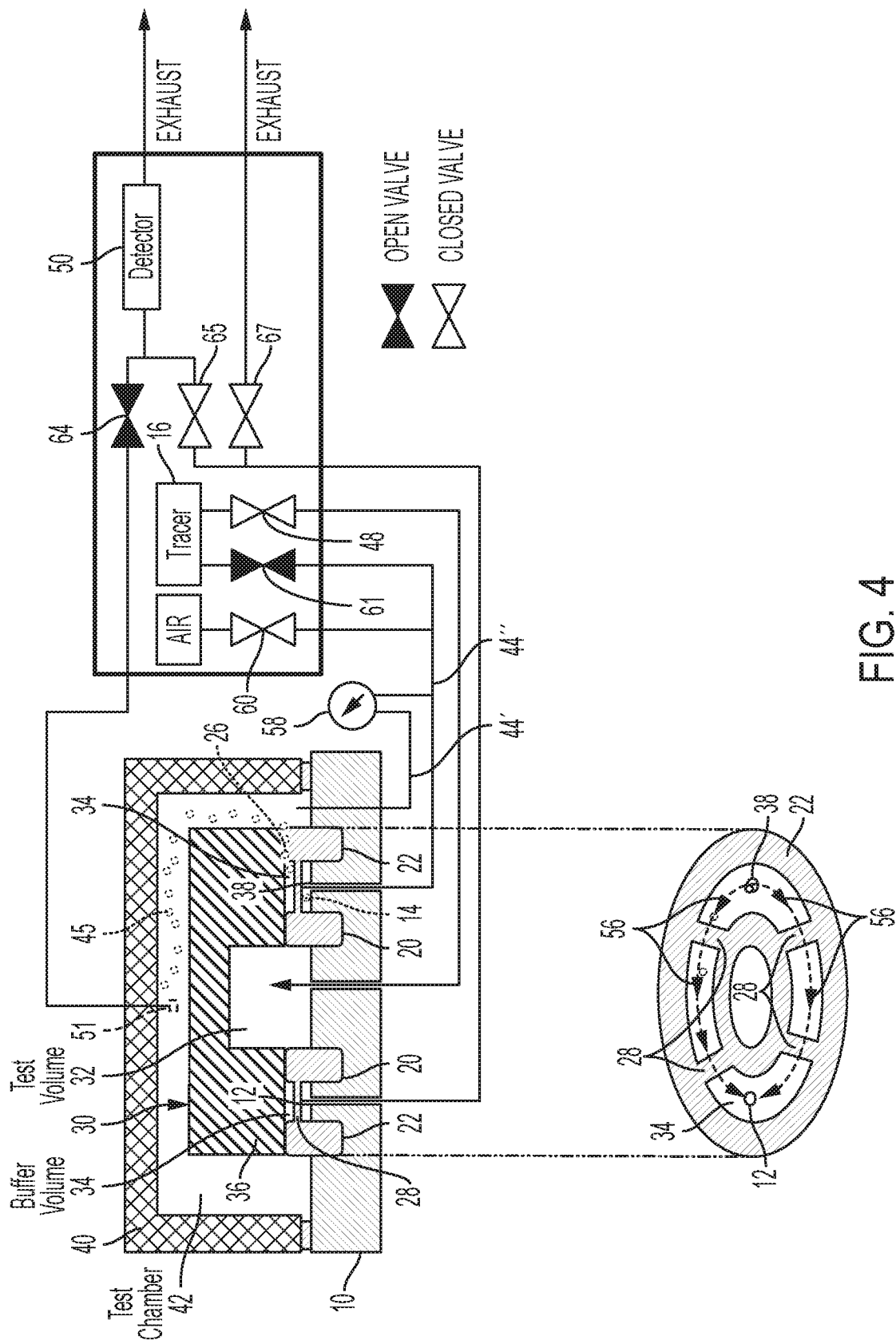
FIG. 4 is a semi-schematic diagram of another example of a leak test apparatus according to the present disclosure.

FIG. 4 is a semi-schematic diagram of another example of a leak test apparatus according to the present disclosure. In an example, as depicted in FIG. 4, the buffer volume 34 and the test chamber 42 are to have a secondary seal 22 pressure differential established therebetween. In examples, establishing the secondary seal pressure differential may include transferring tracer gas into the buffer volume 34 by opening a tracer-to-buffer volume valve 61 connected to a source 16 of the tracer gas. The secondary seal pressure differential urges the tracer gas through a secondary seal leak 26. In the example depicted in FIG. 4, detecting an amount of the tracer gas in the test chamber 42 by the detector 50 and/or detector 51 is indicative of the secondary seal leak 26. In the example depicted in FIG. 4, a differential pressure sensor 58 is connected to flowpaths 44' and 44". Thus, the differential pressure sensor 58 is to quantify a pressure difference (if a pressure difference exists) between the buffer volume 34 and the test chamber 42. The differential pressure sensor 58 may output a differential pressure signal for use by an electronic control system in the apparatus for automatic leak detection according to the present disclosure.

Figure 5:
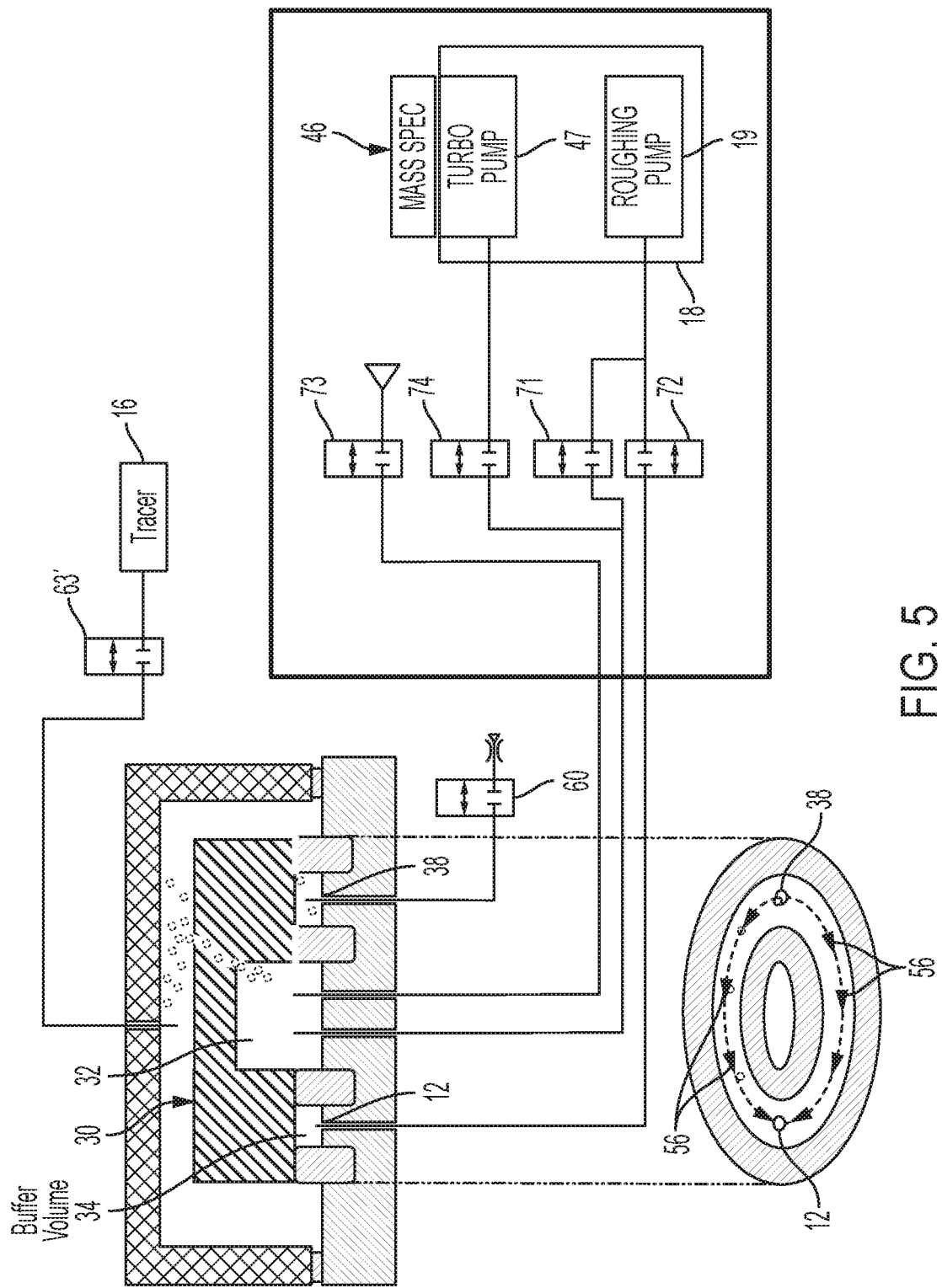
FIG. 5 is a semi-schematic diagram of another example of a leak test apparatus according to the present disclosure.

FIG. 5 is a semi-schematic diagram of another example of a leak test apparatus according to the present disclosure. In an example, as depicted in FIG. 5, the leak test apparatus may include a vacuum pump 18 in fluid communication with the buffer volume 34 for removing the at least a portion of the fixture leakage 14 from the buffer volume 34 by at least partially evacuating the buffer volume 34 via the vacuum pump 18. As disclosed herein, the vacuum pump 18 may be any suitable pump 18. In the example depicted in FIG. 5, the vacuum pump 18 includes a combination of a roughing pump 19 and a turbo pump 47.

As used herein, a roughing pump means a vacuum pump used as a first stage toward achieving a high vacuum or ultra-high vacuum. A roughing pump is to achieve a rough vacuum. As used herein, the term "rough vacuum" means an absolute pressure of about $1\times10^{-3}$ Torr (0.1 Pa). As used herein, the term "high vacuum" means an absolute pressure of about $1\times10^{-3}$ to $1\times10^{-9}$ Torr (0.1 Pa-$1\times10^{-7}$ Pa). As used herein, the term "hard vacuum" means the same as the term "high vacuum." As used herein, the term "ultra-high vacuum" means an absolute pressure of about $1\times10^{-9}$ to $1\times10^{-12}$ Torr ($1\times10^{-7}$ Pa-$1\times10^{-10}$ Pa). As used herein, the term "low vacuum" means an absolute pressure of about 760 to 25 Torr ($1\times10^5$ Pa-$3\times10^3$ Pa). As used herein, atmospheric pressure is about 760 Torr ($1.013\times10^5$ Pa). It is to be understood that typical leaks may prevent the vacuum pump 18 from achieving a rough vacuum or a high vacuum without detracting from the leak detection capabilities of the apparatus and method of the present disclosure. For example, as shown in FIG. 5, an air admittance valve 60 allows atmospheric air or nitrogen gas to enter the buffer volume 34 to flush any tracer gas out of the buffer volume 34 by action of the vacuum pump 18. Such flushing may allow the tracer gas to be removed from the buffer volume more quickly and completely than by using the vacuum pump 18 to achieve a rough vacuum or high vacuum without flushing the buffer volume 34. The air admittance valve 60 may regulate the flow of air or nitrogen gas into the buffer volume 34. As such, a vacuum may be achieved in the buffer volume 34 even when air or nitrogen gas flows into the buffer volume 34 via the air admittance valve 60.

In FIG. 5, the roughing pump 19 is connected to the buffer volume 34 with a buffer volume rough vacuum control valve 72 disposed to regulate a gas flow from the buffer volume 34 into the roughing pump 19. The roughing pump 19 is also connected to the test volume 32 with a test volume rough vacuum control valve 71 disposed to regulate a gas flow from the test volume 32 into the roughing pump 19. A turbo pump 47 may also be connected to the test volume 32 with a test volume turbo vacuum control valve 74 disposed to regulate a gas flow from the test volume 32 into the turbo pump 47. The mass spectrometer 46 may be used to analyze gas pumped from the test volume 32 to determine an amount of tracer gas that may have entered the test volume 32. An air supply valve 73 may be connected on a suction side of the test volume rough vacuum control valve 71 and the test volume turbo vacuum control valve 74 to provide clean air or nitrogen to, for example, flush tracer gas from the turbo pump and mass spectrometer between test runs. As shown in FIG. 5 and FIG. 6, the air supply valve 73 is connected to the test volume 32 to flush all of the vacuum system that is connected to the test volume 32. The air supply valve 73 may be used at the same time as the air admittance valve 60 to allow the buffer volume 34 and the test volume 32 to be evacuated using the same vacuum pump 18.

FIG. 6 is a semi-schematic diagram of another example of a leak test apparatus according to the present disclosure. In an example, as depicted in FIG. 6, the primary seal 20 includes a first lip 21 of a double seal 24, and the secondary seal 22 includes a second lip 23 of the double seal 24. A groove 25 is defined between the first lip 21 and the second lip 23, and the groove 25 defines at least a portion of the buffer volume 34. In examples, the buffer volume 34 may be bounded by the first lip 21, the second lip 23 and the workpiece 30.

In examples, the buffer volume 34 may be bounded by the primary seal 20, the secondary seal 22, the workpiece 30 and the fixture 10 as depicted in FIGS. 2A-2D, FIG. 3, FIG. 4, and FIG. 5. In examples, the primary seal 20 may be attached to the secondary seal 22 by at least a partial web 28 as depicted in FIG. 3 and FIG. 4.

FIG. 7A is a diagram depicting an example of relative pressures in a leak test apparatus as disclosed herein. In FIG. 7A, the test volume 32 is at a higher pressure than the test chamber 42. Thus, the direction of flow 53 is from the test volume 32 to the test chamber 42. Purge gas is flowed into the buffer volume 34 however an offsetting amount of gas is exhausted from the buffer volume 34 so that the gas pressure in the buffer volume remains at atmospheric pressure. The pressure differential between the test volume 32 and the buffer volume 34 drives the tracer gas through a primary seal leak (in the direction of flow arrow 54) if a primary seal leak exists. The buffer volume 34 is at a pressure that is not high enough above the pressure in the test chamber 42 to cause a significant amount of tracer gas to be transferred from the buffer volume 34 through a fixture leak into the test chamber 42. Since the purge gas flushes nearly all of the tracer gas from the buffer volume, and there is a low pressure differential between the buffer volume 34 and the test chamber 42, the amount of tracer gas that passes through the buffer volume 34 into the test chamber 42 is negligible. Thus, the number of false positive leakage test results caused by fixture leaks is minimized.

FIG. 7B is a diagram depicting an example of relative pressures in a leak test apparatus as disclosed herein. In FIG. 7B, the test volume 32 is at a higher pressure than the test chamber 42. In FIG. 7B, the test chamber 42 is at a hard vacuum. Thus, the direction of flow 53 is from the test volume 32 to the test chamber 42. Purge gas is flowed into the buffer volume 34 however an offsetting amount of gas is exhausted from the buffer volume 34 so that the gas pressure in the buffer volume remains at atmospheric pressure. The pressure differential between the test volume 32 and the buffer volume 34 drives the tracer gas through a primary seal leak (in the direction of flow arrow 54) if a primary seal leak exists. Since the purge gas flushes nearly all of the tracer gas from the buffer volume, the amount of tracer gas that passes through the buffer volume 34 into the test chamber 42 is negligible. Thus, the number of false positive leakage test results caused by fixture leaks is minimized.

Figure 8:
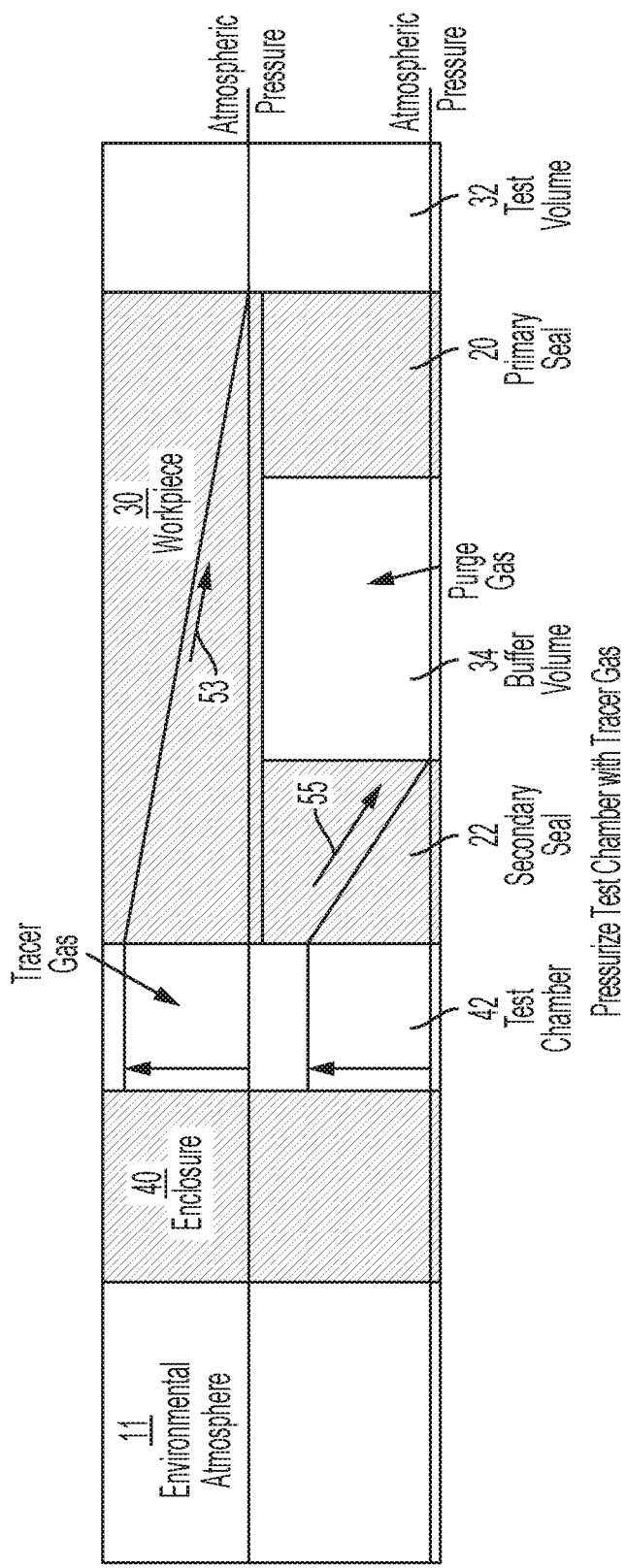
FIG. 8 is a diagram depicting an example of relative pressures in a leak test apparatus as disclosed herein.

FIG. 8 is a diagram depicting an example of relative pressures in a leak test apparatus as disclosed herein. In FIG. 8, the test chamber 42 is at a higher pressure than the test volume 32. Thus, the direction of flow 53 is from the test chamber 42 to the test volume 32. Purge gas is flowed into the buffer volume 34 however an offsetting amount of gas is exhausted from the buffer volume 34 so that the gas pressure in the buffer volume remains at atmospheric pressure. The pressure differential between the test chamber 42 and the buffer volume 34 drives the tracer gas through a secondary seal leak (in the direction of flow arrow 55) if a secondary seal leak exists. The buffer volume 34 is at a pressure that is not high enough above the pressure in the test volume 32 to cause a significant amount of tracer gas to be transferred from the buffer volume 34 through a fixture leak into the test volume 32. Since the purge gas flushes nearly all of the tracer gas from the buffer volume, and there is a low pressure differential between the buffer volume 34 and the test volume 32, the amount of tracer gas that passes through the buffer volume 34 into the test volume 32 is negligible. Thus, the number of false positive leakage test results caused by fixture leaks is minimized.

FIG. 9 is a diagram depicting an example of relative pressures in a leak test apparatus as disclosed herein. In FIG. 9, the test chamber 42 is at a higher pressure than the test volume 32. Thus, the direction of flow 53 is from the test chamber 42 to the test volume 32. The buffer volume 34 is also connected to a vacuum as shown in FIG. 5. Air or a purge gas is flowed into the buffer volume 34 at buffer volume inlet 38. The gas flow entering the buffer volume 34 is controlled to be less than or equal to the gas flow exiting the port 12, thereby maintaining a vacuum in the buffer volume 34. The buffer volume 34 is at a pressure that is not high enough above the pressure in the test volume 32 to cause a significant amount of tracer gas to be transferred from the buffer volume 34 through a fixture leak into the test volume 32. Since the purge gas flushes nearly all of the tracer gas from the buffer volume 34, and there is a low pressure differential between the buffer volume 34 and the test volume 32, the amount of tracer gas that passes through the buffer volume 34 into the test volume 32 is negligible. Thus, the number of false positive leakage test results caused by fixture leaks is minimized.

FIG. 10 is a diagram depicting an example of relative pressures in a leak test apparatus as disclosed herein. In FIG. 10, the test chamber 42 is at a higher pressure than the test volume 32. Thus, the direction of flow 53 is from the test chamber 42 to the test volume 32. FIG. 10 depicts an example to show a primary seal leak. Tracer gas is flowed into the buffer volume 34 at buffer volume inlet 38 as shown in FIG. 4. The pressure differential between the buffer volume 34 and the test volume 32 drives the tracer gas through a primary seal leak (in the direction of flow arrow 54) if a primary seal leak exists. Thus, the apparatus can be used to identify and characterize the severity of a fixture leak due to, for example, wear of the primary seal, before such a primary seal leak becomes too large for the buffer volume and purge process to overcome. The pressure differential between the buffer volume 34 and the test chamber 42 will urge the tracer gas through a secondary seal leak (in the direction of flow arrow 55) if a secondary seal leak exists, however, the pressure difference is not great enough to cause significant flow through a secondary seal leak unless the secondary seal leak is large.

Figure 11:
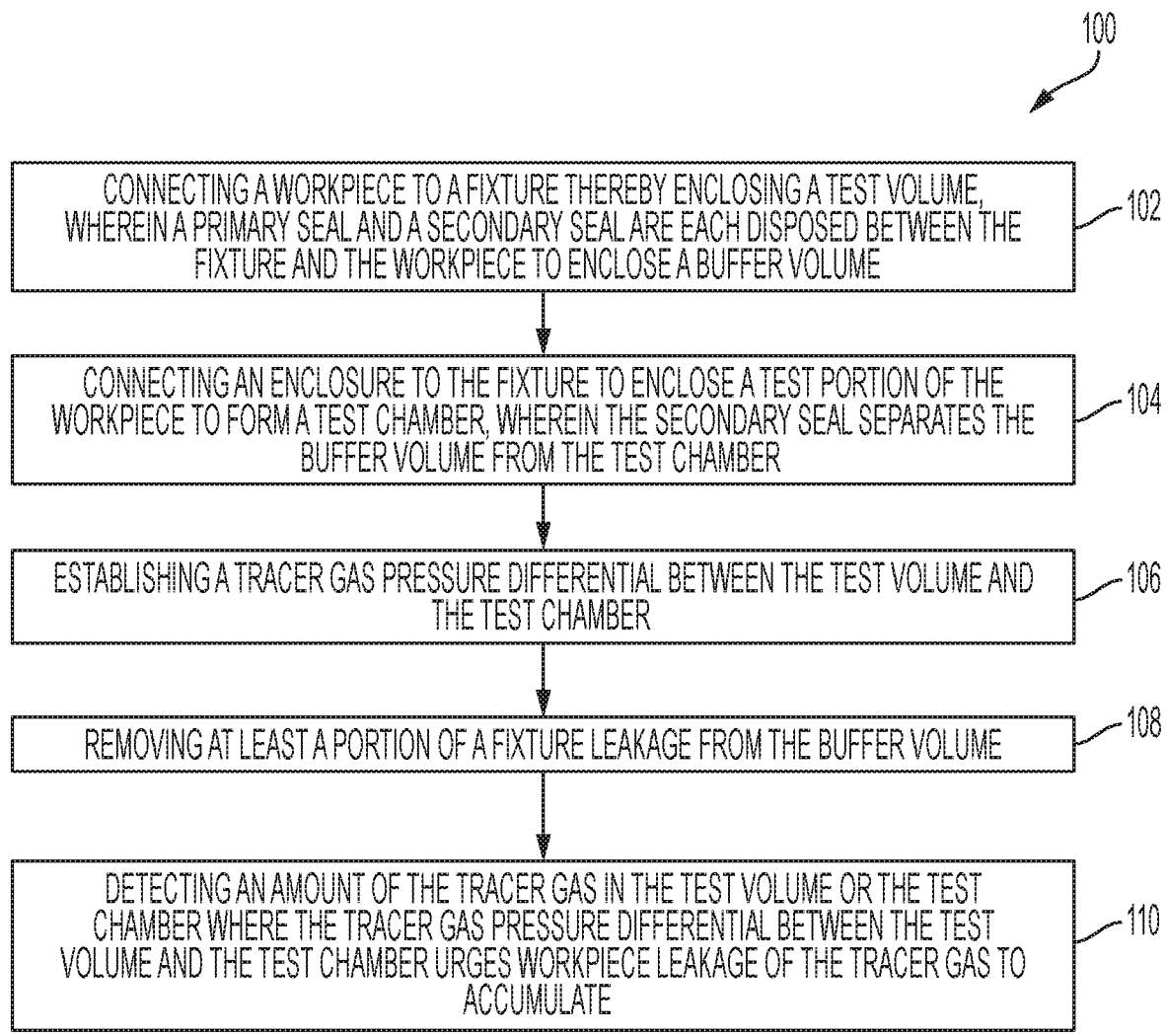
FIG. 11 is a flow chart depicting an example of a method for automatic leak detection according to the present disclosure.

FIG. 11 is a flow chart depicting an example of a method for automatic leak detection 100 according to the present disclosure. As depicted in FIG. 11, an example of a method 100 for automatic leak detection 100, according to the present disclosure includes connecting a workpiece 30 to a fixture 10 thereby enclosing a test volume 32, wherein a primary seal 20 and a secondary seal 22 are each disposed between the fixture 10 and the workpiece 30 to enclose a buffer volume 34 as depicted at box 102. As shown at reference numeral 104, the method 100 includes connecting an enclosure 40 to the fixture 10 to enclose a test portion 36 of the workpiece 30 to form a test chamber 42, wherein the secondary seal 22 separates the buffer volume 34 from the test chamber 42. As shown at reference numeral 106, the method 100 includes establishing a tracer gas pressure differential between the test volume 32 and the test chamber 42. As shown at reference numeral 108, the method 100 includes removing at least a portion of a fixture leakage 14 from the buffer volume 34. As shown at reference numeral 110, the method 100 includes detecting an amount of the tracer gas in the test volume 32 or the test chamber 42 where the tracer gas pressure differential between the test volume 32 and the test chamber 42 urges workpiece leakage 45 of the tracer gas to accumulate. In examples of the method 100, the tracer gas may include helium gas, hydrogen gas, forming gas, or any detectable gas or gas mixture.

In examples of the present disclosure, the method for automatic leak detection 100 according to the present disclosure may further include, using the tracer gas, establishing a secondary seal 22 pressure differential between the buffer volume 34 and the test chamber 42; and detecting an amount of the tracer gas in the test chamber 42 to detect a leak at the secondary seal 22. Detecting an amount of the tracer gas may involve using a mass spectrometer 46. Detecting an amount of the tracer gas may involve using an electronic hydrogen detector 51.

In examples of the method for automatic leak detection 100, an enclosure seal 27 may be disposed between the enclosure 40 and the fixture 10 forming an enclosure-fixture joint 29. The enclosure-fixture joint 29 may have an enclosure-fixture joint 29 leak rate that is smaller than the flow rate of the tracer gas into the test chamber 42. In examples, the enclosure seal 27 may include a brush seal.

In examples of the method 100, the primary seal 20 may include a first lip 21 of a double seal 24, and the secondary seal 22 may include a second lip 23 of the double seal 24. A groove 25 that defines at least a portion of the buffer volume 34 may be defined between the first lip 21 and the second lip 23. In examples of the method 100, the buffer volume 34 may be bounded by the first lip 21, the second lip 23 and the workpiece 30. The buffer volume 34 may be bounded by the primary seal 20, the secondary seal 22, the workpiece 30 and the fixture 10. The primary seal 20 may be attached to the secondary seal 22 by at least a partial web 28. In examples, the establishing the tracer gas pressure differential may include causing the tracer gas pressure to be higher in the test volume 32 than in the test chamber 42. In examples, establishing the tracer gas pressure differential may include transferring tracer gas into the test volume 32 by opening a tracer-to-test volume valve 48 connected to a source 16 of the tracer gas. In examples, establishing the tracer gas pressure differential may include causing the tracer gas pressure to be higher in the test chamber 42 than the test volume 32. In examples, establishing the tracer gas pressure differential may include transferring tracer gas into the test chamber 42 by opening a tracer-to-test chamber valve 63 connected to a source 16 of the tracer gas.

In examples of the method for automatic leak detection 100 according to the present disclosure, removing at least a portion of the fixture leakage 14 from the buffer volume 34 may include flowing a purge gas through the buffer volume 34 to flush at least a portion of the fixture leakage 14 out of the buffer volume 34. Removing at least a portion of the fixture leakage 14 from the buffer volume 34 may include at least partially evacuating the buffer volume 34 via a pump 18.

In examples of the method for automatic leak detection 100 according to the present disclosure may further include, performing a gross leak test. In examples, the gross leak test may be performed at any suitable time. In an example, the gross leak test may be performed before the "establishing a tracer gas pressure differential between the test volume and the test chamber" 106 (FIG. 11). The gross leak test may include using a differential pressure sensor 58 (FIG. 4) to monitor the pressure difference between the buffer volume 34 and the test chamber 42. The differential pressure sensor 58 may alternatively be used to detect a clog in the buffer volume 34. The gross leak test may include using a vacuum pump 18 to withdraw air or another gas or gas mixture from the test chamber 42, test volume 32 or buffer volume 34 with all closable valves closed; and determining (e.g. via a pressure gage) if a rate of change of a pressure in the test chamber 42, test volume 32 or buffer volume 34 is within a predetermined range. In an example, the predetermined range may be suitable to determine integrity of the test setup. For example, if the vacuum pump 18 is unable to create at least a low vacuum in a test chamber 42 having a 1 liter volume in 10 seconds, a gross leak may be present. Remedial steps, for example, resetting the workpiece 30 or enclosure 40, or cleaning the primary seal 20 or the secondary seal 22, may be used to resolve the gross leak before continuing with the method 100.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise. No language in the specification should be construed as indicating any unclaimed element as essential to the practice of the examples.

As used herein, the term "fluid" means a gas, liquid, or combinations thereof.

In describing and claiming the examples disclosed herein, the singular forms "a", "an", and "the" include plural referents unless the context clearly dictates otherwise.

The terms "connect/connected/connection", "attach/attached/attachment" and/or the like are broadly defined herein to encompass a variety of divergent connected arrangements and assembly techniques. These arrangements and techniques include, but are not limited to (1) the direct communication between one component and another component with no intervening components therebetween; and (2) the communication of one component and another component with one or more components therebetween, provided that the one component being "connected to" or "attached to" the other component is somehow in communication with the other component (notwithstanding the presence of one or more additional components therebetween). Additionally, two components may be permanently, semi-permanently, or releasably engaged with and/or connected to one another.

It is to be further understood that "communication" is to be construed to include all forms of communication, including direct and indirect communication. Indirect communication may include communication between two components with additional component(s) located therebetween.

While several examples have been described in detail, it is to be understood that the disclosed examples may be modified. Therefore, the foregoing description is to be considered non-limiting.

What is claimed is:

1. An apparatus for automatic leak detection, comprising:
  a fixture having a primary seal and a secondary seal disposed thereon, wherein the fixture is to connect to a workpiece to enclose a test volume at least partially defined in the workpiece, wherein the primary seal and the secondary seal are to interface with the workpiece to at least partially enclose a buffer volume;
  an enclosure to connect to the fixture to enclose a test portion of the workpiece to form a test chamber, wherein the secondary seal is to separate the buffer volume from the test chamber;
  wherein the test volume and the test chamber are to have a tracer gas pressure differential established therebetween;
  a port in fluid communication with the buffer volume to remove at least a portion of a fixture leakage from the buffer volume; and
  a detector to detect an amount of the tracer gas in the test volume or the test chamber where the tracer gas pressure differential between the test volume and the test chamber urges workpiece leakage of the tracer gas to accumulate;
  wherein the buffer volume is bounded by the primary seal, the secondary seal, the workpiece and the fixture;
  and wherein the primary seal is attached to the secondary seal by at least a partial web.

2. The apparatus of claim 1 wherein the buffer volume and the test chamber are to have a secondary seal pressure differential established therebetween, wherein the secondary seal pressure differential urges the tracer gas through a secondary seal leak, and wherein detecting an amount of the tracer gas in the test chamber by the detector is indicative of the secondary seal leak.

3. The apparatus of claim 1, further comprising a buffer volume inlet in fluid connection with the buffer volume for flowing a purge gas through the buffer volume and out through the port to remove the at least a portion of the fixture leakage from the buffer volume by flushing at least a portion of the fixture leakage out of the buffer volume.

4. The apparatus of claim 1, further comprising a pump in fluid communication with the buffer volume for removing the at least a portion of the fixture leakage from the buffer volume by at least partially evacuating the buffer volume via the pump.

5. The apparatus of claim 1, further comprising a differential pressure sensor in fluid communication with the buffer volume and the test chamber for determining a differential pressure between the buffer volume and the test chamber.

6. The apparatus of claim 1 wherein the tracer gas pressure differential is to be established by causing the tracer gas pressure to be higher in the test volume than in the test chamber.

7. The apparatus of claim 6 wherein the tracer gas pressure differential is to be established by transferring tracer gas into the test volume by opening a tracer-to-test volume valve connected to a source of the tracer gas.

8. An apparatus for automatic leak detection, comprising:
  a fixture having a primary seal and a secondary seal disposed thereon, wherein the fixture is to connect to a workpiece to enclose a test volume at least partially defined in the workpiece, wherein the primary seal and the secondary seal are to interface with the workpiece to at least partially enclose a buffer volume;
  an enclosure to connect to the fixture to enclose a test portion of the workpiece to form a test chamber, wherein the secondary seal is to separate the buffer volume from the test chamber;
  wherein the test volume and the test chamber are to have a tracer gas pressure differential established therebetween;
  a port in fluid communication with the buffer volume to remove at least a portion of a fixture leakage from the buffer volume; and
  a detector to detect an amount of the tracer gas in the test volume or the test chamber where the tracer gas pressure differential between the test volume and the test chamber urges workpiece leakage of the tracer gas to accumulate;
  wherein the test chamber comprises at least two fluidly separate subchambers, wherein the detector is in branched fluid communication with the at least two fluidly separate subchambers via fluid communication branches, and wherein at least one valve opens and closes the fluid communication branches to temporally separate a detector signal associated with each of the at least two fluidly separate subchambers.

9. The apparatus of claim 8 wherein the buffer volume and the test chamber are to have a secondary seal pressure differential established therebetween, wherein the secondary seal pressure differential urges the tracer gas through a secondary seal leak, and wherein detecting an amount of the tracer gas in the test chamber by the detector is indicative of the secondary seal leak.

10. The apparatus of claim 8, further comprising a buffer volume inlet in fluid connection with the buffer volume for flowing a purge gas through the buffer volume and out through the port to remove the at least a portion of the fixture leakage from the buffer volume by flushing at least a portion of the fixture leakage out of the buffer volume.

11. The apparatus of claim 8, further comprising a pump in fluid communication with the buffer volume for removing the at least a portion of the fixture leakage from the buffer volume by at least partially evacuating the buffer volume via the pump.

12. The apparatus of claim 8, further comprising a differential pressure sensor in fluid communication with the buffer volume and the test chamber for determining a differential pressure between the buffer volume and the test chamber.

13. The apparatus of claim 8 wherein the primary seal includes a first lip of a double seal, and the secondary seal includes a second lip of the double seal, wherein a groove is defined between the first lip and the second lip, and wherein the groove defines at least a portion of the buffer volume.

14. The apparatus of claim 13 wherein the buffer volume is bounded by the first lip, the second lip and the workpiece.

15. The apparatus of claim 8 wherein the buffer volume is bounded by the primary seal, the secondary seal, the workpiece and the fixture.

16. The apparatus of claim 15 wherein the primary seal is attached to the secondary seal by at least a partial web.

17. The apparatus of claim 8 wherein the tracer gas pressure differential is to be established by causing the tracer gas pressure to be higher in the test volume than in the test chamber.

18. The apparatus of claim 17 wherein the tracer gas pressure differential is to be established by transferring tracer gas into the test volume by opening a tracer-to-test volume valve connected to a source of the tracer gas.

\* \* \* \* \*